(12) United States Patent
Takeuchi et al.

(10) Patent No.: US 11,867,609 B2
(45) Date of Patent: Jan. 9, 2024

(54) METHOD AND APPARATUS FOR ACCELERATED CORROSION TESTING

(71) Applicant: Nippon Telegraph and Telephone Corporation, Tokyo (JP)

(72) Inventors: Yosuke Takeuchi, Musashino (JP); Takashi Miwa, Musashino (JP); Takuya Kamisho, Musashino (JP); Soichi Oka, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 535 days.

(21) Appl. No.: 17/265,106

(22) PCT Filed: Jun. 28, 2019

(86) PCT No.: PCT/JP2019/025922
§ 371 (c)(1),
(2) Date: Feb. 1, 2021

(87) PCT Pub. No.: WO2020/031546
PCT Pub. Date: Feb. 13, 2020

(65) Prior Publication Data
US 2021/0318228 A1 Oct. 14, 2021

(30) Foreign Application Priority Data
Aug. 6, 2018 (JP) ................................. 2018-147517

(51) Int. Cl.
*G01N 17/00* (2006.01)
*G01N 33/2045* (2019.01)
*G01N 33/38* (2006.01)

(52) U.S. Cl.
CPC ....... *G01N 17/006* (2013.01); *G01N 33/2045* (2019.01)

(58) Field of Classification Search
CPC .... G01N 17/00; G01N 17/002; G01N 33/383; G01N 33/20; G01N 5/04;
(Continued)

(56) References Cited

U.S. PATENT DOCUMENTS 9,267,875 B2 * 2/2016 Yap ...................... G01N 17/002

FOREIGN PATENT DOCUMENTS

| CN | 204491639 U | * | 7/2015 | ............. E02D 19/04 |
| EP | 1148329 A1 | * | 10/2001 | ........... G01N 33/383 |
| JP | 2013044529 A | * | 3/2013 | ............. G01N 17/00 |

OTHER PUBLICATIONS

Toshio Yonezawa et al., *Corrosion Rate of Steel Reinforcements After Carbonation of Concrete*, Architectural Institute of Japan, Structural System Lecture, Journal of Structural and Construction Engineering, vol. 79, No. 704, 2014, pp. 1405-1414.
(Continued)

*Primary Examiner* — Herbert K Roberts
*Assistant Examiner* — Anthony W Megna Fuentes
(74) *Attorney, Agent, or Firm* — Workman Nydegger (57) ABSTRACT

An accelerated corrosion test apparatus includes: a moisture sensor disposed near the reinforcing steel exposed from a cracked portion of concrete; a weight measuring instrument that measures a weight of the reinforced concrete specimen; and a control terminal that is connected both to the moisture sensor and to the weight measuring instrument and controls a temperature and humidity control device, thereby alternately and repeatedly performing a wetting step of supplying moisture to the inside of a crack in the cracked concrete, and a drying step of removing moisture in the inside of the crack and moisture on the exposed surface of the reinforcing steel, wherein the control terminal terminates the wetting step and starts the drying step when moisture is detected in the moisture sensor, or when change in slope of weight change
(Continued)

of the reinforced concrete specimen is detected, after the start of the wetting step.

11 Claims, 7 Drawing Sheets

(58) Field of Classification Search
CPC ............ G01N 2203/024; G01N 33/38; G01N 17/006; G01N 33/2045
See application file for complete search history.

(56) References Cited

OTHER PUBLICATIONS

Takeshi Iyoda et al., *Effect of Existence of Cracks in Concrete on Depth of Carbonation,* Monthly Journal of the Institute of Industrial Science, University of Tokyo, vol. 50, No. 9, 1998, pp. 319-321.

* cited by examiner

METHOD AND APPARATUS FOR ACCELERATED CORROSION TESTING

TECHNICAL FIELD

The present invention relates to a technique of accelerating corrosion of a reinforcing steel contained in a reinforced concrete specimen having cracking.

BACKGROUND ART

Reinforced concrete is also known as a composite material that prevents corrosion of an internal reinforcing steel by covering the reinforcing steel with alkaline concrete, in addition of the role of the internal reinforcing steel in enhancing the strength of the concrete.

Meanwhile, when reinforced concrete is placed in a predetermined environment, carbonation of the concrete proceeds gradually from an atmospheric contact surface by oxygen entry. If the carbonation proceeds to the position of the reinforcing steel, corrosion prevention performance is lost so that the internal reinforcing steel of the concrete falls into a state in which corrosion starts. For this reason, RC structures, etc. are evaluated for their in-service periods on the basis of the length of time to start corrosion of a reinforcing steel by carbonation of concrete (Non-Patent Literature 1).

Particularly, it has been reported that upon cracking of concrete, carbonation of the concrete proceeds according to the depth of the cracking from the concrete surface (Non-Patent Literature 2). Although the cracking of concrete is a fatal defect for the structure of reinforced concrete, it is difficult to foresee or prevent this cracking. Usually, measures to immediately repair or renew reinforced concrete upon confirmation of cracking are taken. Cracking is detected by visual inspection. Time intervals of inspection depend largely on the number of target structures and the operation of maintenance and inspection manpower. Thus, cracking is presumably left for a given period after its occurrence.

Accordingly, there is currently a demand for determining beforehand the deterioration state of a reinforced concrete structure ascribable to reinforcing steel corrosion after occurrence of cracking.

CITATION LIST

Non-Patent Literature

Non-Patent Literature 1: Yonezawa, et al., "Study on corrosion rate of reinforcing steel after carbonation of concrete", Transactions of Architectural Institute of Japan (AIJ). Journal of structural and construction engineering, Vol. 79, No. 704, October 2014, p. 1405-1414

Non-Patent Literature 2: Iyota, et al., "Effect of Existence of Cracks in Concrete on Depth of Carbonation", Monthly journal of the Institute of Industrial Science, University of Tokyo, Vol. 50, No. 9, September 1998, p. 319-321

SUMMARY OF THE INVENTION

Technical Problem

For determining beforehand the deterioration state of a reinforced concrete structure ascribable to reinforcing steel corrosion after occurrence of cracking, it is necessary to corrode an internal reinforcing steel of reinforced concrete in a short period. However, guidelines have not yet provided to a method for corroding a reinforcing steel of a reinforced concrete specimen having cracking in a short period. There has existed neither an accelerated corrosion test method specialized for reinforced concrete specimens nor a device therefor.

The present invention has been made in light of the situation described above. An object of the present invention is to accelerate corrosion of a reinforcing steel contained in a reinforced concrete specimen having cracking.

Means for Solving the Problem

The accelerated corrosion test method of the present invention is an accelerated corrosion test method wherein corrosion of a reinforcing steel contained in a reinforced concrete specimen having cracking is accelerated, wherein a control terminal is connected both to a moisture sensor disposed near the reinforcing steel exposed from the cracked portion of the concrete, and to a weight measuring instrument that measures a weight of the reinforced concrete specimen, and controls a moisture supply and removal device, thereby alternately and repeatedly performing a wetting step of supplying moisture to the inside of a crack in the cracked concrete, and a drying step of terminating the wetting step and removing moisture in the inside of the crack and moisture on the exposed surface of the reinforcing steel when moisture is detected in the moisture sensor, or when change in slope of weight change of the reinforced concrete specimen is detected, after the start of the wetting step.

In the accelerated corrosion test method, the control terminal terminates the drying step and starts the wetting step when moisture is no longer detected in the moisture sensor, or when the weight of the reinforced concrete specimen is decreased by an amount corresponding to the increment in weight when the change in slope of weight change has been detected, after the start of the drying step.

In the accelerated corrosion test method, the control terminal regards an increased weight of the reinforced concrete specimen as a moisture content in the inside of the crack, and terminates the wetting step when change in slope of change in the moisture content in the inside of the crack is detected instead of the detection of the change in slope of weight change of the reinforced concrete specimen, or when the moisture content in the inside of the crack reaches a saturated moisture content based on an internal volume of the crack.

In the accelerated corrosion test method, the control terminal terminates the drying step when the moisture content in the inside of the crack is decreased by an amount corresponding to the saturated moisture content.

In the accelerated corrosion test method, in the wetting step, the reinforced concrete specimen is immersed in water, or moisture is sprayed to the reinforced concrete specimen.

The accelerated corrosion test apparatus of the present invention is an accelerated corrosion test apparatus that accelerates corrosion of a reinforcing steel contained in a reinforced concrete specimen having cracking, comprising: a moisture sensor disposed near the reinforcing steel exposed from the cracked portion of the concrete; a weight measuring instrument that measures a weight of the reinforced concrete specimen; and a control terminal that is connected both to the moisture sensor and to the weight measuring instrument and controls a moisture supply and removal device, thereby alternately and repeatedly performing a wetting step of supplying moisture to the inside of a crack in the cracked concrete, and a drying step of removing moisture in the inside of the crack and moisture on the exposed surface of the reinforcing steel, wherein the control terminal terminates the wetting step and starts the drying step when moisture is detected in the moisture sensor, or when change in slope of weight change of the reinforced concrete specimen is detected, after the start of the wetting step.

In the accelerated corrosion test apparatus, the control terminal terminates the drying step and starts the wetting step when moisture is no longer detected in the moisture sensor, or when the weight of the reinforced concrete specimen is decreased by an amount corresponding to the increment in weight when the change in slope of weight change has been detected, after the start of the drying step.

In the accelerated corrosion test apparatus, the control terminal regards an increased weight of the reinforced concrete specimen as a moisture content in the inside of the crack, and terminates the wetting step and starts the drying step when change in slope of change in the moisture content in the inside of the crack is detected instead of the detection of the change in slope of weight change of the reinforced concrete specimen, or when the moisture content in the inside of the crack reaches a saturated moisture content based on an internal volume of the crack, and terminates the drying step and starts the wetting step when the moisture content in the inside of the crack is decreased by an amount corresponding to the saturated moisture content.

Effects of the Invention

According to the present invention, corrosion of a reinforcing steel contained in a reinforced concrete specimen having cracking can be accelerated.

DESCRIPTION OF EMBODIMENTS

A feature of the present invention is that in order to accelerate corrosion of a reinforcing steel contained in a reinforced concrete specimen having cracking, a wetting step of supplying moisture to the inside of a crack in the concrete, and a drying step of removing moisture in the inside of the crack and moisture on the exposed surface of the reinforcing steel are repeated.

In the inside of reinforced concrete having cracking, when a crack reaches the reinforcing steel through carbonation of the concrete of a cracked inner wall, the neighborhood of the reinforcing steel also has neutral conditions. Since environmental moisture is almost neutral, corrosion of the reinforcing steel proceeds upon entry of the moisture to the inside of the crack. However, if moisture remains in the inside of the crack for a given period, diffusion of oxygen is inhibited due to corrosion products or the moisture, or the neighborhood of the reinforcing steel is alkalized by diffusion of calcium hydroxide from the concrete. Therefore, the progression of corrosion is stopped. Hence, for accelerating corrosion of a reinforcing steel at a cracking position, it is necessary to inhibit alkalization of moisture in the inside of the crack, or to supply oxygen.

Accordingly, the present invention is directed to interfering with retention of moisture in the inside of a crack in order to inhibit alkalization of moisture in the inside of the crack and to accelerate supply of oxygen. Specifically, moisture in the inside of the crack is removed by applying the drying step to the reinforced concrete specimen having cracking. Further, subsequent re-entry of moisture and re-drying are repeated. In this respect, reduction in time of the accelerated corrosion test is attained by alternately making switch between the wetting step and the drying step at the time of detection of saturation or disappearance of a moisture content in the inside of the crack by estimating the moisture content in the inside of the crack, or at the time of detection of the presence or absence of moisture in the inside of the cracked concrete in a moisture sensor.

Hereinafter, one mode for carrying out the present invention will be described with reference to the drawings.

Figure 1:
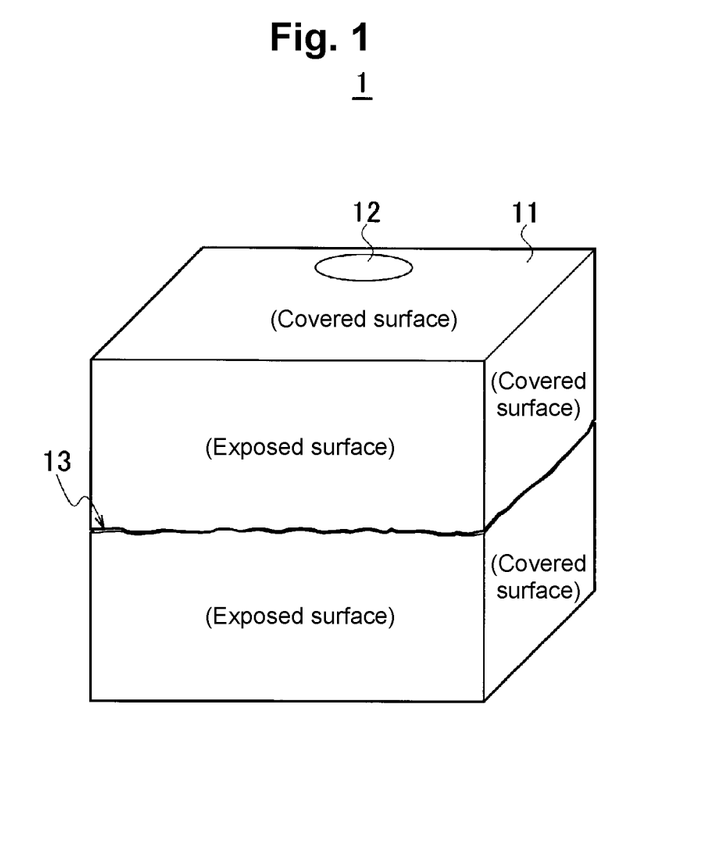
FIG. 1 is a diagram showing the appearance of a reinforced concrete specimen.

FIG. 1 is a diagram showing the appearance of reinforced concrete specimen 1 used in the present embodiment. The reinforced concrete specimen 1 is configured, as shown in FIG. 1, to have concrete 11 in a cuboid form, and reinforcing steel 12 in a cylindrical form disposed perpendicularly in the inside of the concrete 11. In the concrete 11, cracked portion 13 is formed so as to crack the concrete in a direction perpendicular to the up-down direction of the reinforcing steel 12.

For such reinforced concrete specimen 1, it is desirable to cover a concrete surface except for a front exposed surface with a resin or the like in order to mimic the reinforced concrete structure in the actual environment. The type of the resin for use in the covering is desirably a resin low permeable to moisture, for example, epoxy resin. The thickness of the covering is desirably 1 mm or larger.

Figure 2:
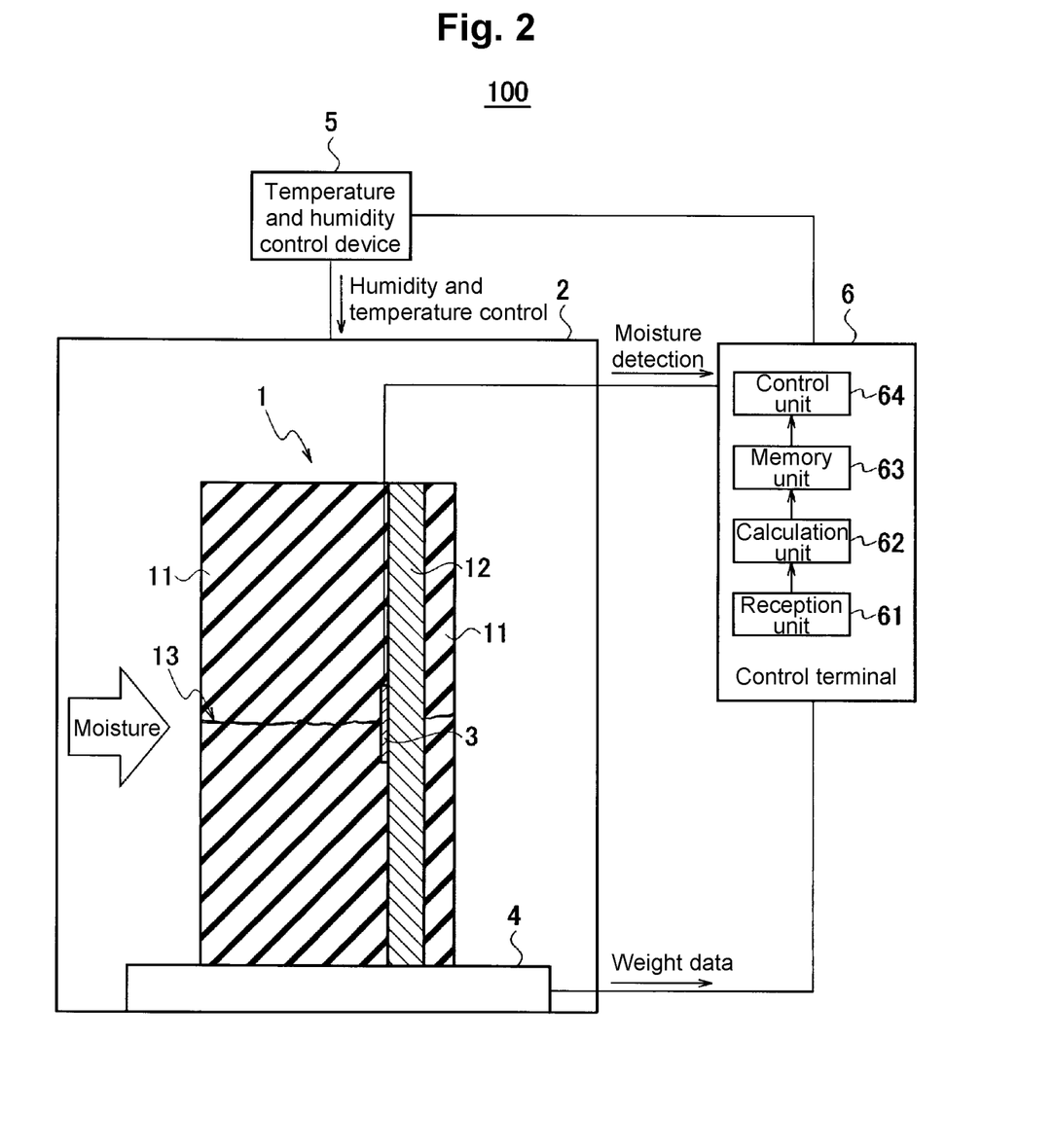
FIG. 2 is a diagram showing the configuration of an accelerated corrosion test apparatus.

FIG. 2 is a diagram showing the configuration of accelerated corrosion test apparatus 100 according to the present embodiment. The reinforced concrete specimen 1 is shown with its cross section taken along the depth direction of FIG. 1. As shown in FIG. 2, the accelerated corrosion test apparatus 100 is configured to have the reinforced concrete specimen 1 shown in FIG. 1 as well as test vessel 2, moisture sensor 3, weight measuring instrument 4, temperature and humidity control device 5, and control terminal 6.

The test vessel 2 is a containment device which contains the reinforced concrete specimen 1. For keeping an intra-vessel temperature and humidity constant, the test vessel 2 desirably has a structure that can hermetically seal the reinforced concrete specimen 1.

Figure 3:
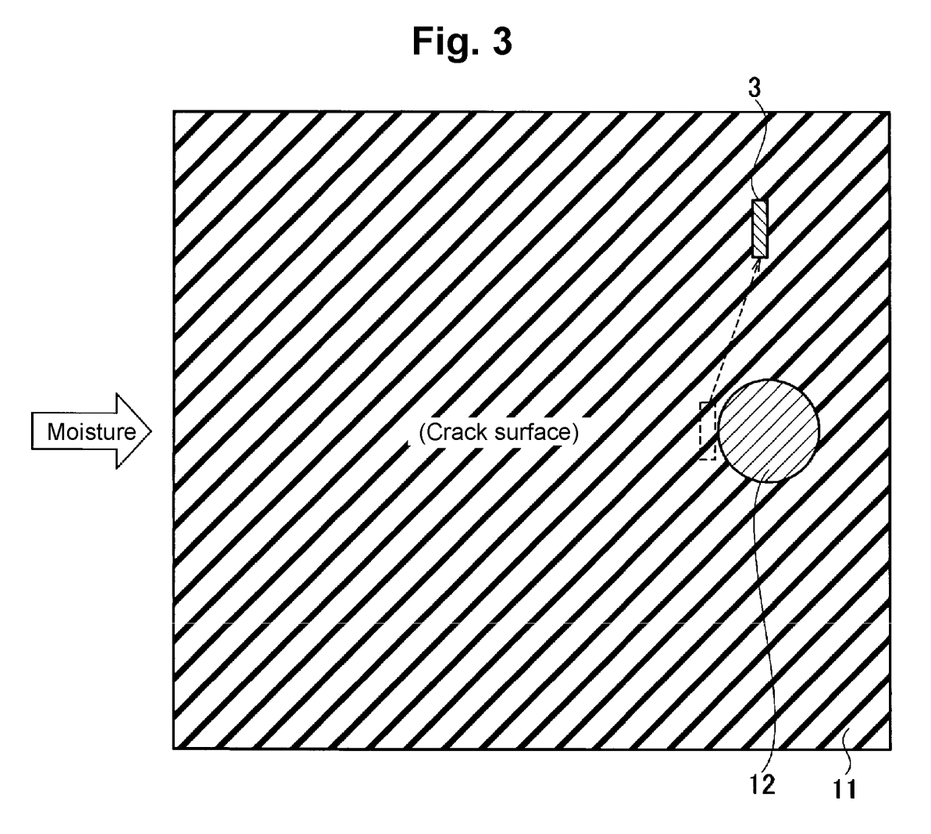
FIG. 3 is a diagram showing exemplary disposition of a moisture sensor.

The moisture sensor 3 is disposed near the reinforcing steel 12 exposed from the cracked portion 13 in the reinforced concrete specimen 1, and has a function of outputting a moisture detection signal indicating the presence of moisture in the inside of a crack to the control terminal 6 when moisture in the inside of the crack is detected. The moisture sensor 3 is disposed adjacently to the reinforcing steel 12 in order to measure a moisture content on the exposed surface of the reinforcing steel 12. Such adjacent disposition might have an adverse effect on accelerated corrosion of the reinforcing steel 12. Therefore, as shown in FIG. 3, the moisture sensor 3 may be disposed at a neighboring position within a given distance from the reinforcing steel 12. The housing material of the moisture sensor 3 is desirably ceramic or plastic so as not to influence corrosion of the reinforcing steel 12.

The weight measuring instrument 4 is disposed beneath the reinforced concrete specimen 1 in the inside of the test vessel 2, and has a function of measuring a weight of the reinforced concrete specimen 1 and sending the measured weight data to the control terminal 6.

The temperature and humidity control device 5 has a function of controlling each of the internal temperature and humidity of the test vessel 2 on the basis of a control signal from the control terminal 6. For example, an air conditioner capable of adjusting each of temperature and humidity, a fan with communication functions, a sprayer with communication functions, or a water supply and discharge device with communication functions is used as the temperature and humidity control device 5. The temperature and humidity control device 5 corresponds to the "moisture supply and removal device" described in the scope of claims.

The control terminal 6 is electrically and physically connected to all of the moisture sensor 3, the weight measuring instrument 4, and the temperature and humidity control device 5, and configured, as shown in FIG. 2, to have reception unit 61, calculation unit 62, memory unit 63, and control unit 64. The control terminal 6 is constituted by a computer, for example, a personal computer.

The reception unit 61 has a function of receiving each of a moisture detection signal from the moisture sensor 3 and weight data from the weight measuring instrument 4.

The calculation unit 62 has a function of performing estimate calculation in which an increased weight of the reinforced concrete specimen 1 is regarded as a moisture content in the inside of the crack, using the weight data on the reinforced concrete specimen 1 measured in the weight measuring instrument 4, and allowing the calculation results to be stored in the memory unit 63.

The memory unit 63 has a function of storing the moisture content in the inside of the crack after the start of the test estimate-calculated in the calculation unit 62, as intra-crack moisture content data associated with the time of the test, and also storing the arbitrary preset number of test cycles in order to repeatedly perform the wetting step and the drying step.

The control unit 64 has a function of sending a control signal to the temperature and humidity control device 5 and controlling the temperature and humidity control device 5, thereby alternately and repeatedly performing the wetting step of supplying moisture to the inside of the crack in the reinforced concrete specimen 1 within the test vessel 2, and the drying step of removing moisture in the inside of the crack and moisture on the exposed surface of the reinforcing steel 12.

The control unit 64 also has a function of terminating the wetting step and starting the drying step when moisture is detected in the moisture sensor 3 after the start of the wetting step, and terminating the drying step and starting the wetting step when moisture is no longer detected in the moisture sensor 3.

The control unit 64 also has a function of terminating the wetting step and starting the drying step when change in slope of weight change of the reinforced concrete specimen 1 is detected after the start of the wetting step, and terminating the drying step and starting the wetting step when the weight of the reinforced concrete specimen 1 is decreased by an amount corresponding to the increment in weight when the change in slope of weight change of the reinforced concrete specimen 1 has been detected, after the start of the drying step.

The control unit 64 also has a function of terminating the wetting step and starting the drying step when change in slope of change in the moisture content in the inside of the crack is detected with reference to the intra-crack moisture content data stored in the memory unit 63, or when the moisture content in the inside of the crack (moisture content in the inside of the crack estimate-calculated from the weight change of the reinforced concrete specimen 1) reaches a saturated moisture content based on an internal volume of the crack, and terminating the drying step and starting the wetting step when the moisture content in the inside of the crack is decreased by an amount corresponding to the saturated moisture content.

The control unit 64 may employ only any one of or two or more in combinations of the presence or absence of a moisture detection signal from the moisture sensor 3, weight change of the reinforced concrete specimen 1, and change in moisture content in the inside of the crack estimated on the basis of the weight of the reinforced concrete specimen 1.

Figure 4:
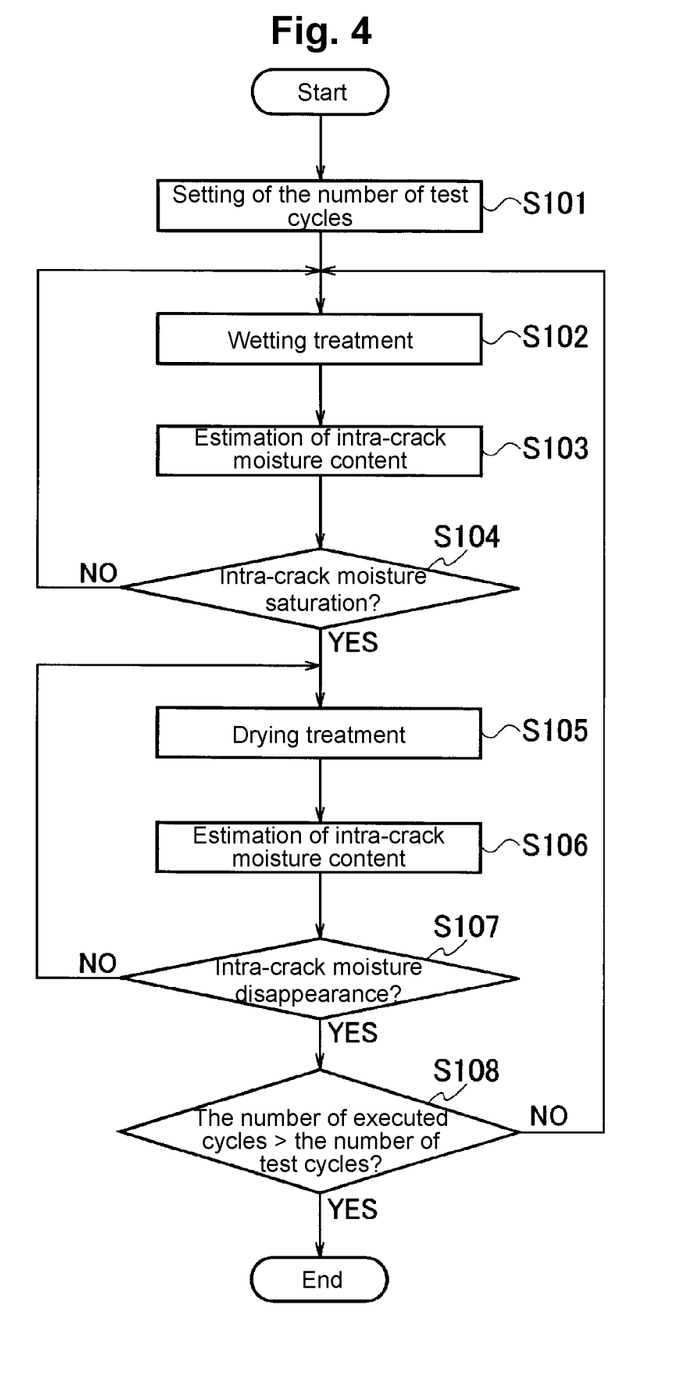
FIG. 4 is a diagram showing the process flow of an accelerated corrosion test method.

Next, an accelerated corrosion test method which is performed using the accelerated corrosion test apparatus 100 will be described. FIG. 4 is a diagram showing the process flow of the accelerated corrosion test method. In the present embodiment, the accelerated corrosion test apparatus 100 accelerates corrosion of the reinforcing steel 12 contained in the reinforced concrete specimen 1 by repeating the wetting step and the drying step arbitrary times for the reinforced concrete specimen 1.

Step S101;

First, the control terminal 6 determines the number of test cycles. The number of test cycles for use in the test may be the number of test cycles stored in the memory unit 63, or may be the number of test cycles input by a user at the start of the test.

Step S102 (Wetting Step);

In the case of leaving the reinforced concrete specimen 1 in the atmospheric environment for the first time, the control terminal 6 starts supply of moisture to the reinforced concrete specimen 1 which is in a relatively dry state. For example, the control terminal 6 uses the temperature and humidity control device 5 to humidify the inside of the test vessel 2. In addition, the control terminal 6 may use a water supply and discharge device to supply water to the test vessel 2 so that the reinforced concrete specimen 1 is immersed in water, and to discharge the water, or may use a sprayer to spray moisture to the cracked portion 13. The control terminal 6 may supply salt water instead of the moisture in order to further accelerate corrosion of the reinforcing steel 12.

Step S103 (Wetting Step);

Subsequently, the control terminal 6 performs estimate calculation in which an increased weight of the reinforced concrete specimen 1 is regarded as a moisture content in the inside of the crack, using the weight data on the reinforced concrete specimen 1 sent from the weight measuring instrument 4 after the start of the test, and allowing the calculation results to be stored in association with the time of the test.

Step S104 (Wetting Step);

Subsequently, the control terminal 6 determines whether or not the inside of the crack is suffused with moisture. The process proceeds to step S105 by terminating the supply of moisture started in the step S102 when the inside of the crack is suffused with moisture, and goes back to the step S102 to continue the supply of moisture when the inside of the crack is not suffused with moisture.

In principle, corrosion occurs upon arrival of moisture on the surface of the reinforcing steel 12. Therefore, the arrival of moisture on the surface of the reinforcing steel 12 is the time when the wetting step is terminated. Hereinafter, a specific example thereof will be described.

For example, in the case of using the moisture sensor 3, the control terminal 6 determines that the inside of the crack is suffused with moisture, when receiving a moisture detection signal from the moisture sensor 3.

In the case of using the weight measuring instrument 4, the control terminal 6 may employ a slope of weight change of the reinforced concrete specimen 1 and, in this case, determines that the inside of the crack is suffused with moisture, when change in the slope of weight change is detected. Specifically, the weight of the reinforced concrete specimen 1 is increased at a given increase ratio from the start of supply of moisture to saturation of moisture in the inside of the crack. Since the increase ratio is decreased after saturation, the control terminal 6 determines that moisture arrives on the surface of the reinforcing steel 12 so that the inside of the crack is suffused with moisture, when change in slope of weight increase of the reinforced concrete specimen 1 is detected.

Likewise, in the case of using the weight measuring instrument 4, the control terminal 6 may employ the moisture content in the inside of the crack estimate-calculated in the step S103 and, in this case, determines that the inside of the crack is suffused with moisture, when change in slope of change in the moisture content in the inside of the crack (=change in slope of weight change of the reinforced concrete specimen 1) is detected, or when the moisture content in the inside of the crack reaches a saturated moisture content based on an internal volume of the crack (the inside of the crack is filled with moisture).

In the case of using the weight measuring instrument 4, it is determined that moisture arrives on the surface of the reinforcing steel 12 so that the inside of the crack is suffused with moisture, when the weight of the reinforced concrete specimen 1 having, for example, a crack width of 0.1 mm, a width of 100 mm, and a depth of 50 mm is increased by 500 mg, or when the moisture content in the inside of the crack is increased by 500 mg.

Step S105 (Drying Step);

Then, the control terminal 6 starts removal of moisture in the inside of the crack and moisture on the exposed surface of the reinforcing steel 12. For example, the control terminal 6 uses the temperature and humidity control device 5 to dry the inside of the test vessel 2. In addition, the control terminal 6 may use a fan to wind the cracked portion 13.

Step S106 (Drying Step);

Subsequently, the control terminal 6 performs, as in the step S103, estimate calculation in which an decreased weight of the reinforced concrete specimen 1 is regarded as a moisture content in the inside of the crack, using the weight data on the reinforced concrete specimen 1 sent from the weight measuring instrument 4 after the start of the test, and allowing the calculation results to be stored in association with the time of the test.

Step S107 (Drying Step);

Subsequently, the control terminal 6 determines whether or not moisture has been removed from the inside of the crack. The process proceeds to step S108 when moisture has been removed from the inside of the crack, and goes back to the step S105 to continue the removal of moisture when moisture has not yet been removed from the inside of the crack.

For example, in the case of using the moisture sensor 3, the control terminal 6 determines that moisture has been removed from the inside of the crack, when no longer receiving a moisture detection signal from the moisture sensor 3.

In the case of using the weight measuring instrument 4, the control terminal 6 may employ a slope of weight change of the reinforced concrete specimen 1 and, in this case, determines that moisture has been removed from the inside of the crack, when the weight of the reinforced concrete specimen 1 is decreased by an amount corresponding to the increment in weight when the change in slope of weight change of the reinforced concrete specimen 1 has been detected.

Likewise, in the case of using the weight measuring instrument 4, the control terminal 6 may employ the moisture content in the inside of the crack estimate-calculated in the step S106 and, in this case, determines that moisture has been removed from the inside of the crack, when the moisture content in the inside of the crack is decreased by an amount corresponding to the saturated moisture content.

Step S108;

Finally, the control terminal 6 determines whether or not the number of executed cycles of the test exceeds the number of test cycles. The process is terminated when the number of executed cycles exceeds the number of test cycles, and goes back to the step S102 when the number of executed cycles does not exceed the number of test cycles.

Figure 5:
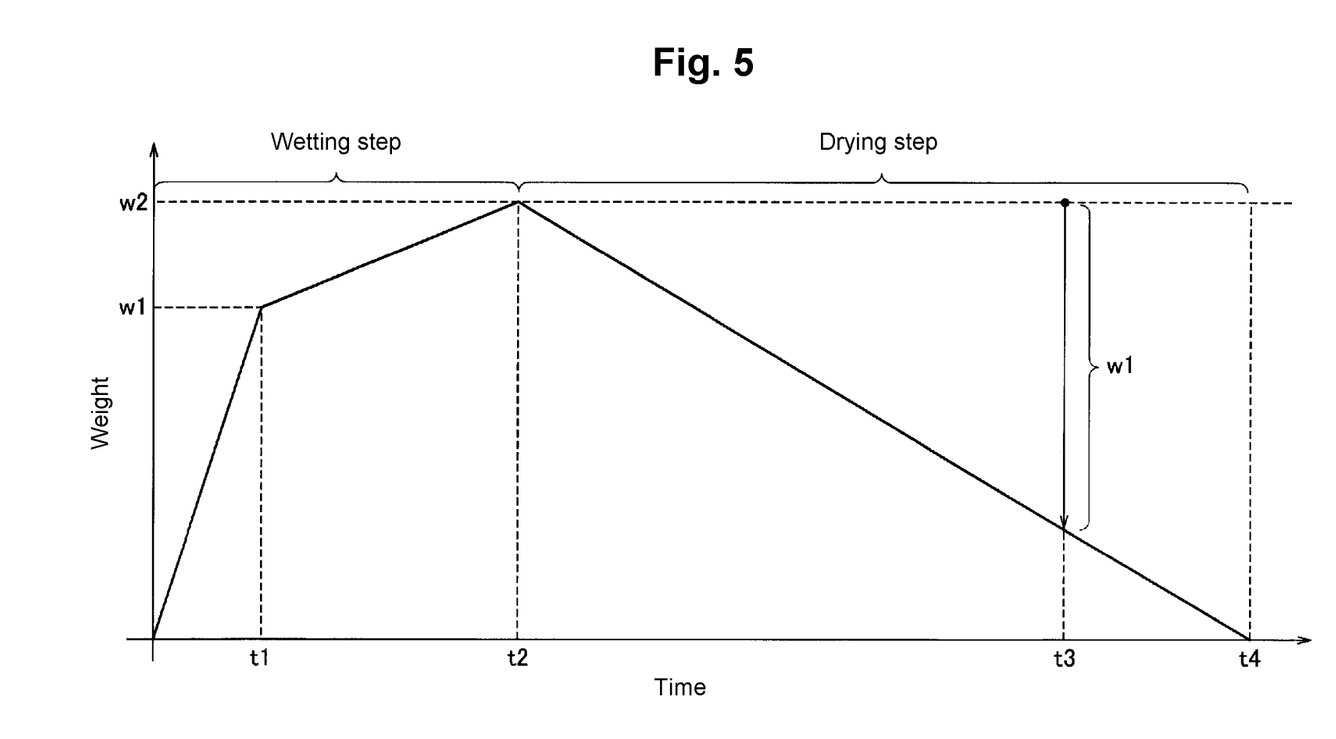
FIG. 5 is a diagram showing exemplary weight change of the reinforced concrete specimen.

FIG. 5 is a diagram showing exemplary weight change of the reinforced concrete specimen 1.

When moisture enters the reinforced concrete specimen 1, moisture entry to the inside of the crack proceeds rapidly. On the other hand, after suffusing of the inside of the crack with moisture, diffusion of moisture into the concrete becomes rate-limiting so that the weight changes slowly. Hence, the reinforced concrete specimen 1 in a dry state is subjected to salt water spraying, humidification, immersion in a solution, etc., and an increased weight of the reinforced concrete specimen 1 is measured. Weight w1 at time t1 when change in slope of weight change is detected is regarded as an intra-crack saturated moisture content. Since it is necessary to detect change in slope of weight change, weight w2 after change in slope of the weight and time t2 thereof are shown in FIG. 5. As the wetting step is continued after the time t1, the diffusion of moisture to the inside of the concrete proceeds to continue weight increase. Supply of moisture beyond the weight w1 is unnecessary. Therefore, the time required for the wetting step can be optimized by terminating the wetting step when the weight is increased to the weight w1, not the weight w2, or when the time is the time t1, not the time t2.

For the drying step, it is necessary to decrease at least the increment in weight corresponding to the weight w1. However, in the drying step, moisture in the inside of the crack and moisture in the inside of the concrete evaporate at the same time from the exposed surface. Therefore, for removing moisture in the inside of the crack, it is necessary to remove a weight or a moisture content that attains w1≤w2. In the case of using a time, it is necessary to attain t3≤t4. When the time when the wetting step is terminated is the time t1, not the time t2, or when the increased weight in the wetting step is the weight w1, not the weight w2, the drying and wetting steps can be optimized by setting the time when the drying step is terminated to time t3 or the decreased weight in the drying step to the weight w1.

Figure 6:
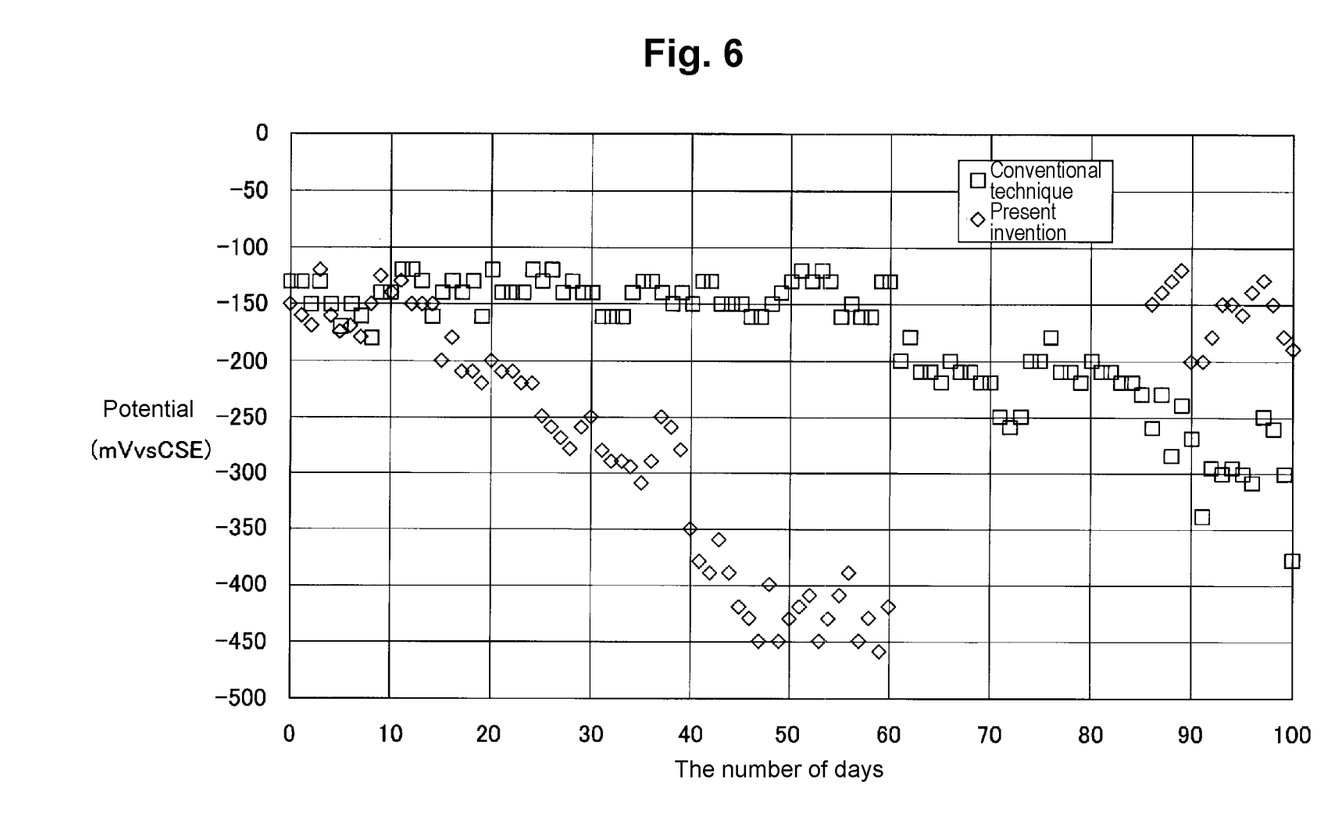
FIG. 6 is a diagram showing results of measuring a potential of a reinforcing steel during corrosion and after corrosion.

FIG. 6 is a diagram showing results of measuring a potential of the reinforcing steel 12 during corrosion and after corrosion. The open squares depict the results about a conventional technique, and the open rhombuses depict the results about the present invention. The drying step (intra-vessel humidity: 0%) and the wetting step (intra-vessel humidity: 100%) were alternately and repeatedly performed for 12 hours each of the steps. When the potential of the reinforcing steel 12 was measured using a corrosion determination device (ASTM-C876), the potential after a lapse of 40 to 60 days was −450 to −350 mVvsCSE for the present invention and −100 to −150 mVvsCSE for the conventional technique. As is evident from the measurement results, the time to decrease the potential is shorter in the present invention than in the conventional technique. Hence, the reinforcing steel 12 was found to corrode in a short time according to the present invention.

Figure 7:
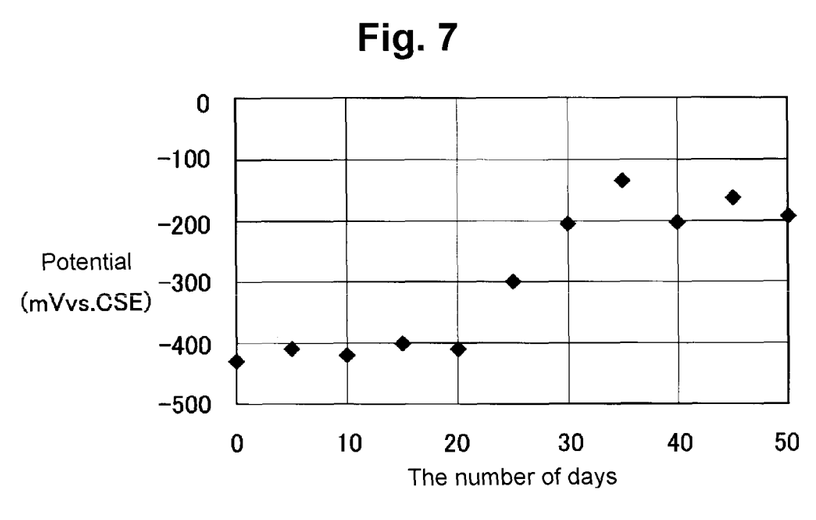
FIG. 7 is a diagram showing results of measuring a potential of a reinforcing steel after corrosion and atmospheric exposure.

FIG. 7 is a diagram showing results of measuring a potential of the reinforcing steel 12 after the accelerated corrosion test of the present invention and subsequent atmospheric exposure of the reinforcing steel 12. The potential decreased by the accelerated corrosion test is elevated by the atmospheric exposure, indicating that moisture in the inside of the crack is not sufficiently dried off at the time of atmospheric exposure and remains, so that corrosion is stopped.

Thus, according to the present embodiment, accelerated corrosion test apparatus 100 that accelerates corrosion of reinforcing steel 12 contained in reinforced concrete specimen 1 having cracking comprises: moisture sensor 3 disposed near the reinforcing steel 12 exposed from cracked portion 13 of concrete 11; weight measuring instrument 4 that measures a weight of the reinforced concrete specimen 1; and control terminal 6 that is connected both to the moisture sensor 3 and to the weight measuring instrument 4, and controls temperature and humidity control device 5, thereby alternately and repeatedly performing a wetting step of supplying moisture to the inside of a crack in the cracked concrete, and a drying step of removing moisture in the inside of the crack and moisture on the exposed surface of the reinforcing steel 12, wherein the control terminal 6 terminates the wetting step and starts the drying step when moisture is detected in the moisture sensor 3, or when change in slope of weight change of the reinforced concrete specimen 1 is detected, after the start of the wetting step. The time required for the accelerated corrosion test involving corrosion of the reinforcing steel 12 can be reduced, and information contributing to understanding beforehand the deterioration state of a reinforced concrete structure ascribable to reinforcing steel corrosion after occurrence of cracking can be obtained in a short period.

Finally, the control terminal 6 can also be achieved by a computer and a program. The program may be recorded in a recording medium or may be provided through the network.

REFERENCE SIGNS LIST

1 Reinforced concrete specimen
11 Concrete
12 Reinforcing steel
13 Cracked portion
2 Test vessel
3 Moisture sensor
4 Weight measuring instrument
5 Temperature and humidity control device
6 Control terminal
61 Reception unit
62 Calculation unit
63 Memory unit
64 Control unit

The invention claimed is:

1. An accelerated corrosion test method wherein corrosion of a reinforcing steel contained in a reinforced concrete specimen having a crack with an inside that extends to the reinforcing steel so as to expose a surface of the reinforcing steel is accelerated, wherein
a control terminal is connected both to a moisture sensor contained within the reinforced concrete specimen, and to a weight measuring instrument that measures a weight of the reinforced concrete specimen, and controls a moisture supply and removal device, thereby alternately and repeatedly performing:
a wetting step of supplying a moisture to the inside of the crack in the reinforced concrete specimen so that the moisture extends to the exposed surface of the reinforcing steel; and
a drying step of terminating the wetting step and removing the moisture in the inside of the crack and the moisture on the exposed surface of the reinforcing steel when the moisture is detected in the moisture sensor, or when change in slope of weight change of the reinforced concrete specimen is detected, after the start of the wetting step.

2. The accelerated corrosion test method according to claim 1, wherein the control terminal terminates the drying step and starts the wetting step when moisture is no longer detected in the moisture sensor, or when the weight of the reinforced concrete specimen is decreased by an amount corresponding to the increment in weight when the change in slope of weight change has been detected, after the start of the drying step.

3. The accelerated corrosion test method according to claim 2, wherein in the wetting step, the reinforced concrete specimen is immersed in water, or moisture is sprayed to the reinforced concrete specimen.

4. The accelerated corrosion test method according to claim 1, wherein the control terminal regards an increased weight of the reinforced concrete specimen as a moisture content in the inside of the crack, and terminates the wetting step when change in slope of change in the moisture content in the inside of the crack is detected instead of the detection of the change in slope of weight change of the reinforced concrete specimen, or when the moisture content in the inside of the crack reaches a saturated moisture content based on an internal volume of the crack.

5. The accelerated corrosion test method according to claim 4, wherein the control terminal terminates the drying step when the moisture content in the inside of the crack is decreased by an amount corresponding to the saturated moisture content.

6. The accelerated corrosion test method according to claim 5, wherein in the wetting step, the reinforced concrete specimen is immersed in water, or moisture is sprayed to the reinforced concrete specimen.

7. The accelerated corrosion test method according to claim 4, wherein in the wetting step, the reinforced concrete specimen is immersed in water, or moisture is sprayed to the reinforced concrete specimen.

8. The accelerated corrosion test method according to claim 1, wherein in the wetting step, the reinforced concrete specimen is immersed in water, or moisture is sprayed to the reinforced concrete specimen.

9. An accelerated corrosion test apparatus that accelerates corrosion of a reinforcing steel contained in a reinforced concrete specimen having a crack with an inside that extends to the reinforcing steel so as to expose a surface of the reinforcing steel, comprising:

a moisture sensor disposed within the reinforced concrete specimen;

a weight measuring instrument that measures a weight of the reinforced concrete specimen; and a control terminal that is connected both to the moisture sensor and to the weight measuring instrument and controls a moisture supply and removal device, the control terminal being configured to alternately and repeatedly perform a wetting step of supplying a moisture to the inside of the crack in the reinforced concrete specimen so that the moisture extends to the exposed surface of the reinforcing steel, and a drying step of removing the moisture in the inside of the crack and the moisture on the exposed surface of the reinforcing steel, wherein the control terminal terminates the wetting step and starts the drying step when the moisture is detected in the moisture sensor, or when change in slope of weight change of the reinforced concrete specimen is detected, after the start of the wetting step.

10. The accelerated corrosion test apparatus according to claim 9, wherein the control terminal terminates the drying step and starts the wetting step when moisture is no longer detected in the moisture sensor, or when the weight of the reinforced concrete specimen is decreased by an amount corresponding to the increment in weight when the change in slope of weight change has been detected, after the start of the drying step.

11. The accelerated corrosion test apparatus according to claim 9, wherein the control terminal regards an increased weight of the reinforced concrete specimen as a moisture content in the inside of the crack, and terminates the wetting step and starts the drying step when change in slope of change in the moisture content in the inside of the crack is detected instead of the detection of the change in slope of weight change of the reinforced concrete specimen, or when the moisture content in the inside of the crack reaches a saturated moisture content based on an internal volume of the crack, and terminates the drying step and starts the wetting step when the moisture content in the inside of the crack is decreased by an amount corresponding to the saturated moisture content.

* * * * *